United States Patent
He et al.

(10) Patent No.: US 11,034,653 B2
(45) Date of Patent: Jun. 15, 2021

(54) CRYSTAL FORM OF ESTROGEN RECEPTOR INHIBITOR AND PREPARATION METHOD THEREFOR

(71) Applicants: LUOXIN PHARMACEUTICAL (SHANGHAI) CO., LTD., Shanghai (CN); SHANDONG LUOXIN PHARMACEUTICAL GROUP STOCK CO., LTD., Shandong (CN)

(72) Inventors: Huijun He, Shanghai (CN); Jianyu Lu, Shanghai (CN); Weidong Li, Shanghai (CN); Shenyi Shi, Shanghai (CN); Zhijuan Chen, Shanghai (CN); Charles Z. Ding, Shanghai (CN); Lihong Hu, Shanghai (CN); Tie-Lin Wang, Shanghai (CN); Jiaqiang Dong, Shanghai (CN)

(73) Assignees: LUOXIN PHARMACEUTICAL (SHANGHAI) CO., LTD., Shanghai (CN); SHANDONG LUOXIN PHARMACEUTICAL GROUP STOCK CO., LTD., Shandong (CN)

( * ) Notice: Subject to any disclaimer, the term of this patent is extended or adjusted under 35 U.S.C. 154(b) by 0 days.

(21) Appl. No.: 16/648,943

(22) PCT Filed: Sep. 25, 2018

(86) PCT No.: PCT/CN2018/107324
§ 371 (c)(1),
(2) Date: Mar. 19, 2020

(87) PCT Pub. No.: WO2019/057201
PCT Pub. Date: Mar. 28, 2019

(65) Prior Publication Data
US 2020/0247748 A1 Aug. 6, 2020

(30) Foreign Application Priority Data
Sep. 25, 2017 (CN) .......................... 201710874782.5

(51) Int. Cl.
*C07D 209/18* (2006.01)
(52) U.S. Cl.
CPC ........ *C07D 209/18* (2013.01); *C07B 2200/13* (2013.01)
(58) Field of Classification Search
CPC .................................................. C07D 209/18
See application file for complete search history.

(56) References Cited

U.S. PATENT DOCUMENTS

| 10,519,143 B2 | 12/2019 | Lu |
| 2013/0231333 A1 | 9/2013 | Smith |
| 2015/0258099 A1 | 9/2015 | Hager |

FOREIGN PATENT DOCUMENTS

| CN | 103189361 A | 7/2013 |
| CN | 106488767 A | 3/2017 |
| WO | 2012037411 A2 | 3/2012 |
| WO | 2015136016 A2 | 9/2015 |
| WO | 2017162206 A1 | 9/2017 |

OTHER PUBLICATIONS

Andiliy Lai et al., "Identification of GDC-0810 (ARN-810), an Orally Bioavailable Selective Estrogen Receptor Degrader (SERD) that Demonstrates Robust Activity in Tamoxifen-Resistant Breast Cancer Xenografts", J. Med. Chem. 2015, 58 (12), 4888-4904, Apr. 16, 2015.
Dec. 28, 2018 International Search Report issued in International Patent Application No. PCT/CN2018/107324.
Dec. 28, 2018 Written Opinion of the International Searching Authority issued in International Patent Application PCT/CN2018/107324.

*Primary Examiner* — Shawquia Jackson
(74) *Attorney, Agent, or Firm* — Dilworth IP, LLC

(57) ABSTRACT

Disclosed are a crystal form of an estrogen receptor inhibitor and a preparation method therefor, in particular disclosed are a crystal form A of a compound of formula (I) and a preparation method therefor, and the use of the crystal form in the preparation of a drug for treating breast cancer.

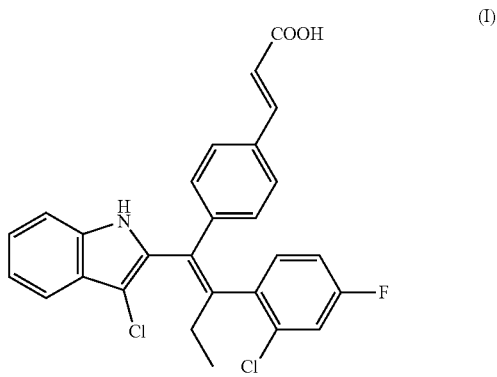

12 Claims, 4 Drawing Sheets

CRYSTAL FORM OF ESTROGEN RECEPTOR INHIBITOR AND PREPARATION METHOD THEREFOR

This application claims the priority to Application No. 201710874782.5, filed on Sep. 25, 2017.

FIELD OF INVENTION

The present invention discloses a crystal form of estrogen receptor inhibitor and preparation method therefor, specifically discloses a crystal form A of a compound of formula (I) and preparation method therefor, and also includes a use of the crystal form in preparing a medicament for treating breast cancer.

PRIOR ARTS

According to the statistics of WHO, breast cancer has become the second most prevalent cancer in the world and has the highest incidence among women. After years of research, the role of the estrogen-estrogen receptor signaling pathway in breast cancer development has already been identified; and the estrogen receptor (ER) has also developed into the most important biomarker for breast cancer. Taking estrogen receptor expression as a discriminative index, breast cancer can be divided into estrogen receptor-positive breast cancer and estrogen receptor-negative breast cancer; wherein estrogen receptor-positive breast cancer accounts for more than 70% of the total number of breast cancer patients.

Endocrine Therapy (ET) targeting the estrogen-estrogen receptor signaling pathway in breast cancer cells has become the first choice for treating estrogen receptor-positive breast cancer because of its minimal harm and significant effect. Endocrine therapy mainly includes the following three treatment methods: ovarian suppression therapy, aromatase inhibitor (AI), and selective estrogen receptor modulator (SERM). Due to its unsatisfactory efficacy and low patient satisfaction, the ovarian suppression therapy is less commonly used than the other two treatment methods. Early aromatase inhibitors (first and second generation) had low target selectivity and large toxic and side effects. After many years of research, the third-generation aromatase inhibitors have been widely used since their selectivity has been greatly unproved, which solved the problem of the early aromatase inhibitors. Among them, letrozole and the like have been used as first-line drugs for the treatment of estrogen receptor-positive breast cancer. Selective estrogen receptor modulators (SERMs) directly act on estrogen receptors to block this signaling pathway, which has a significant effect and a long history of application. Among them, tamoxifen is the most representative selective estrogen receptor modulator. As a first-line drug recommended for priority use, tamoxifen has shown significant clinical efficacy in the prevention and treatment of estrogen receptor-positive breast cancer.

Although the aromatase inhibitor letrozole and the selective estrogen receptor modulator tamoxifen have shown good efficacy in the treatment of estrogen receptor-positive breast cancer, with the application of the two types of drugs, the drug resistance problem of estrogen receptor-positive breast cancer to aromatase inhibitors and selective estrogen receptor modulators has also become increasingly prominent. A large amount of studies have shown that the resistance mechanisms of breast cancer to these two hormone therapies are not exactly the same. For aromatase inhibitors, the estrogen receptor can be mutated accordingly. The mutated estrogen receptor can maintain an excited conformation in the absence of estrogen, allowing it to continue to perform the receptor function to promote breast cancer cell proliferation. The resistance mechanism of breast cancer cells to the selective estrogen receptor modulator tamoxifen is complex and diverse. First, breast cancer cells can compensate for the loss of function of estrogen receptor activation functional domain-2 (AF-2) caused by tamoxifen through activating the function of estrogen receptor activation functional domain-1 (AF-1). At the same time, breast cancer cells can adjust the structure or concentration of the estrogen receptor co-activator to adapt to the conformation of the estrogen receptor bound to tamoxifen, resulting in the recovery of the function of the estrogen receptor, thereby producing drug resistance.

Selective estrogen receptor down-regulator (SERD) has shown its unique superiority in the treatment of breast cancer resistant to the above two hormone therapies. Mechanistically, selective estrogen receptor down-regulators antagonize the function of estrogen receptor, which can greatly accelerate the ubiquitination degradation of estrogen receptors in breast cancer cells (normal or mutated) and completely block estrogen/estrogen receptor signaling pathway, thereby achieving the purpose of inhibiting the growth and proliferation of normal or drug-resistant breast cancer cells. Studies have shown that selective estrogen receptor down-regulators can effectively inhibit the proliferation of hormone-resistant breast cancer cells. Fulvestrant, which is the only commercially available selective estrogen receptor down-regulator, has shown good effects in the treatment of hormone-resistant breast cancer, confirming the unique advantages of selective estrogen receptor down-regulators. However, fulvestrant itself has many problems. First, because of its poor PK properties, fulvestrant shows zero oral bioavailability; meanwhile, fulvestrant has a higher blood clearance. For these two reasons, this drug can only be administered by intramuscular injection. However, due to its strong lipophilic structure, fulvestrant administered by intramuscular injection also has serious problems in terms of tissue distribution; its clinical realization is that only about 50% of breast cancer patients who use fulvestrant have shown a clinical response. Therefore, the development of selective estrogen receptor down-regulators with oral bioavailability is an urgent medical requirement.

WO2012037411 A2 reported an oral selective estrogen receptor down-regulator ARN-810, and a phase II clinical trial of this molecule in the treatment of ER-positive breast cancer is ongoing. According to reports [J. Med. Chem. 2015, 58 (12), 4888-4904], the important pharmacophore of the molecule is the indazole structure on the left side of the molecule, and the nitrogen atoms in the indazole structure bind to the estrogen receptor as a hydrogen bond acceptor.

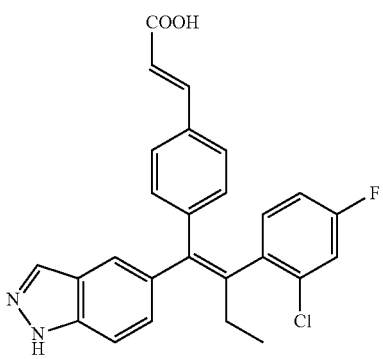

ARN-810

CONTENT OF THE PRESENT INVENTION

The present invention provides crystal form A of a compound of formula (I), characterized by X-ray powder diffraction pattern having characteristic diffraction peaks at the following 2θ angles: 9.921±0.2°, 11.949±0.2°, 14.895±0.2°, 16.753±0.2°, 19.713±0.2°, 20.9±0.2°, 22.45±0.2°, and 23.78±0.2°.

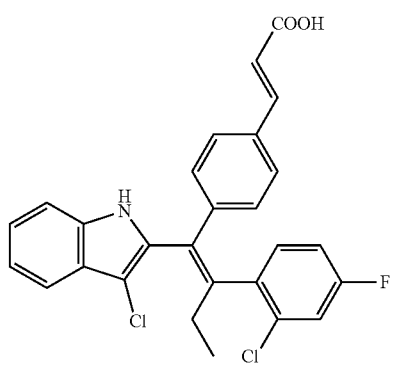

(I)

In some embodiments of the present invention, the X-ray powder diffraction pattern of the crystal form A has characteristic diffraction peaks at the following 2θ angles: 9.921±0.2°, 10.751±0.2°, 11.949±0.2°, 14.169±0.2°, 14.895±0.2°, 16.753±0.2°, 19.713±0.2°, 20.268±0.2°, 20.9±0.2°, 22.45±0.2°, 23.78±0.2°, and 24.39±0.2°.

In some embodiments of the present invention, the X-ray powder diffraction pattern of the crystal form A is shown in FIG. 1.

In some embodiments of the present invention, the analysis data of the XRPD pattern of the crystal form A is shown in Table 1.

TABLE 1

| No. | 2θ angle (°) | Interplanar distance (Å) | Relative Intensity (%) |
|---|---|---|---|
| 1 | 8.836 | 9.9989 | 10.8 |
| 2 | 9.626 | 9.1808 | 24.7 |
| 3 | 9.921 | 8.9085 | 100 |
| 4 | 10.751 | 8.2222 | 23 |
| 5 | 11.229 | 7.8732 | 19.3 |
| 6 | 11.949 | 7.4004 | 33.7 |
| 7 | 12.709 | 6.9597 | 14.6 |

TABLE 1-continued

| No. | 2θ angle (°) | Interplanar distance (Å) | Relative Intensity (%) |
|---|---|---|---|
| 8 | 13.816 | 6.4043 | 13.7 |
| 9 | 14.169 | 6.2453 | 32.5 |
| 10 | 14.383 | 6.1531 | 12.5 |
| 11 | 14.895 | 5.9429 | 79.7 |
| 12 | 15.31 | 5.7826 | 17.8 |
| 13 | 15.924 | 5.5608 | 19.6 |
| 14 | 16.383 | 5.4062 | 10.8 |
| 15 | 16.753 | 5.2877 | 73.7 |
| 16 | 17.322 | 5.115 | 15.7 |
| 17 | 18.63 | 4.7588 | 21.3 |
| 18 | 18.946 | 4.6803 | 14.4 |
| 19 | 19.458 | 4.5582 | 20.7 |
| 20 | 19.713 | 4.4998 | 37.4 |
| 21 | 20.268 | 4.3779 | 34.8 |
| 22 | 20.9 | 4.2469 | 53.8 |
| 23 | 21.355 | 4.1574 | 17.9 |
| 24 | 22.135 | 4.0126 | 12.6 |
| 25 | 22.457 | 3.9558 | 66.7 |
| 26 | 22.849 | 3.8888 | 25.5 |
| 27 | 23.326 | 3.8103 | 15 |
| 28 | 23.78 | 3.7386 | 73.6 |
| 29 | 24.39 | 3.6464 | 32.2 |
| 30 | 25.003 | 3.5584 | 29.5 |
| 31 | 26.288 | 3.3873 | 18.2 |
| 32 | 27.055 | 3.293 | 20.2 |
| 33 | 27.309 | 3.263 | 17.9 |
| 34 | 28.516 | 3.1276 | 20.3 |
| 35 | 29.208 | 3.055 | 9.3 |
| 36 | 30.316 | 2.9458 | 12.4 |
| 37 | 31.228 | 3.8618 | 5.1 |
| 38 | 31.873 | 2.8054 | 5.4 |
| 39 | 33.218 | 2.6948 | 28.3 |
| 40 | 33.863 | 2.6449 | 10.7 |
| 41 | 34.241 | 2.6166 | 7.4 |
| — | — | — | — |

In some embodiments of the present invention, the differential scanning calorimetric curve of the crystal form A has an endothermic peak at 195.45° C.±3° C.

In some embodiments of the present invention, the differential scanning calorimetric curve pattern of the crystal form A is shown in FIG. 2.

In some embodiments of the present invention, the thermogravimetric curve of the crystal form A has a weight loss of 0.1919%±0.2% at 191.73±3° C.

In some embodiments of the present invention, the thermogravimetric curve is shown in FIG. 3.

In some embodiments of the present invention, the preparation method for the crystal form A comprises:
(a) adding the compound of formula (I) to a solvent, stirring, heating, refluxing, naturally cooling to 10° C. to 25° C. after dissolution;
(b) filtering, washing the filter cake with a solvent;
(c) vacuum drying at 50° C.;
wherein the solvent is selected from methanol, ethanol or isopropanol.

In some embodiments of the present invention, the preparation method for the crystal form A comprises:
(a) adding the compound of formula (I) to a solvent, stirring, heating, refluxing, naturally cooling to 10° C. to 25° C. after dissolution;
(b) filtering, washing the filter cake with a solvent;
(c) vacuum drying at 50° C.;
wherein the solvent is selected from a mixed solvent of methanol and water.

In some embodiments of the present invention, the preparation method for the crystal form A comprises:
(a) adding the compound of formula (I) to a solvent, stirring, heating, refluxing, naturally cooling to 10° C. to 25° C. after dissolution;

(b) filtering, washing the filter cake with a solvent;
(c) vacuum drying at 50° C.;
wherein the solvent is selected from a mixed solvent of ethanol and water.

In some embodiments of the present invention, the preparation method for the crystal form A comprises:
(a) adding the compound of formula (I) to a solvent, stirring, heating, refluxing, naturally cooling to 10° C. to 25° C. after dissolution;
(b) filtering, washing the filter cake with a solvent;
(c) vacuum drying at 50° C.;
wherein the solvent is selected from a mixed solvent of isopropanol and water.

In some embodiments of the present invention, the volume ratio of methanol to water in the mixed solvent is 1-4:1.

In some embodiments of the present invention, the volume ratio of methanol to water in the mixed solvent is 1:1.

The present invention also provides a use of the above mentioned crystal form A or the crystal form prepared by the above mentioned method in preparation of a medicament for treating breast cancer.

In some embodiments of the present invention, the X-ray powder diffraction pattern of the crystal form A disposed and sampled (0 day) under the condition of 40° C., 75% RH is shown in FIG. 5.

In some embodiments of the present invention, the analysis data of the XPRD pattern of the crystal form A disposed and sampled (0 day) under the condition of 40° C., 75% RH is shown in Table 2.

TABLE 2

0 day under the conditions of 40° C., 75% RH

| No. | 2θ angle (°) | Interplanar distance (Å) | Relative intensity (%) |
|---|---|---|---|
| 1 | 8.636 | 9.9989 | 10.8 |
| 2 | 9.626 | 9.1808 | 24.7 |
| 3 | 9.921 | 8.9085 | 100 |
| 4 | 10.331 | 8.5555 | 5.7 |
| 5 | 10.751 | 8.2222 | 23 |
| 6 | 11.229 | 7.8732 | 19.3 |
| 7 | 11.949 | 7.4004 | 33.7 |
| 8 | 12.709 | 6.9597 | 14.6 |
| 9 | 13.083 | 6.7616 | 6.1 |
| 10 | 13.816 | 6.4043 | 13.7 |
| 11 | 14.169 | 6.2453 | 32.5 |
| 12 | 14.383 | 6.1531 | 12.5 |
| 13 | 14.895 | 5.9429 | 79.7 |
| 14 | 15.31 | 5.7826 | 17.8 |
| 15 | 15.924 | 5.5608 | 19.6 |
| 16 | 16.383 | 5.4062 | 10.8 |
| 17 | 16.753 | 5.2877 | 73.7 |
| 18 | 17.322 | 5.115 | 15.7 |
| 19 | 17.544 | 5.0508 | 6.6 |
| 20 | 18.63 | 4.7588 | 21.3 |
| 21 | 18.946 | 4.6803 | 14.4 |
| 22 | 19.458 | 4.5582 | 20.7 |
| 23 | 19.713 | 4.4998 | 37.4 |
| 24 | 20.268 | 4.3779 | 34.8 |
| 25 | 20.9 | 4.2469 | 53.8 |
| 26 | 21.355 | 4.1574 | 17.9 |
| 27 | 22.135 | 4.0126 | 12.6 |
| 28 | 22.457 | 3.9558 | 66.7 |
| 29 | 22.849 | 3.8888 | 25.5 |
| 30 | 23.326 | 3.8103 | 15 |
| 31 | 23.78 | 3.7386 | 73.6 |
| 32 | 24.39 | 3.6464 | 32.2 |
| 33 | 25.003 | 3.5584 | 29.5 |
| 34 | 26.288 | 3.3873 | 18.2 |
| 35 | 27.055 | 3.293 | 20.2 |
| 36 | 27.309 | 3.263 | 17.9 |
| 37 | 28.516 | 3.1276 | 20.3 |
| 38 | 28.835 | 3.0936 | 12.2 |
| 39 | 29.208 | 3.055 | 9.3 |
| 40 | 29.663 | 3.0092 | 4.7 |
| 41 | 30.316 | 2.9458 | 12.4 |
| 42 | 30.593 | 2.9198 | 5.9 |
| 43 | 30.968 | 2.8852 | 5.3 |
| 44 | 31.228 | 2.8618 | 5.1 |
| 45 | 31.873 | 2.8054 | 5.4 |
| 46 | 33.218 | 2.6048 | 28.3 |
| 47 | 33.863 | 2.6449 | 10.7 |
| 48 | 34.241 | 2.6166 | 7.4 |
| 49 | 35.979 | 2.4941 | 6.8 |
| 50 | 36.214 | 2.4784 | 4.2 |
| 51 | 38.249 | 2.3511 | 5.8 |

In some embodiments of the present invention, the X-ray powder diffraction pattern of the crystal form A disposed and sampled (10 days) under the condition of 40° C., 75% RH is shown in FIG. 6.

In some embodiments of the present invention, the analysis data of the XPRD pattern of the crystal form A disposed and sampled (10 days) under the condition of 40° C., 75% RH is shown in Table 3.

TABLE 3

10 days under the conditions of 40° C., 75% RH

| No. | 2θ angle (°) | Interplanar distance (Å) | Relative intensity (%) |
|---|---|---|---|
| 1 | 8.798 | 10.043 | 13.6 |
| 2 | 9.632 | 9.1753 | 23.5 |
| 3 | 9.941 | 8.8903 | 100 |
| 4 | 10.299 | 8.5823 | 12.9 |
| 5 | 10.751 | 8.2222 | 27 |
| 6 | 11.286 | 7.8333 | 25.7 |
| 7 | 11.977 | 7.3831 | 35.5 |
| 8 | 12.688 | 6.9707 | 25.5 |
| 9 | 13.105 | 6.7499 | 9.5 |
| 10 | 13.871 | 6.3789 | 19.6 |
| 11 | 14.188 | 6.2371 | 31.8 |
| 12 | 14.389 | 6.1504 | 13.4 |
| 13 | 14.896 | 5.9421 | 100 |
| 14 | 15.263 | 5.8002 | 23 |
| 15 | 15.959 | 5.5487 | 20.2 |
| 16 | 16.718 | 5.2985 | 92.3 |
| 17 | 17.288 | 5.125 | 24.1 |
| 18 | 17.581 | 5.0404 | 9.2 |
| 19 | 18.672 | 4.7483 | 24.7 |
| 20 | 19.01 | 4.6646 | 20.2 |
| 21 | 19.387 | 4.5748 | 28.7 |
| 22 | 19.757 | 4.4898 | 51 |
| 23 | 20.237 | 4.3845 | 50.5 |
| 24 | 20.886 | 4.2496 | 78.2 |
| 25 | 21.24 | 4.1795 | 23.6 |
| 26 | 22.486 | 3.9508 | 96.9 |
| 27 | 22.898 | 3.8806 | 45.1 |
| 28 | 23.355 | 3.8057 | 16.5 |
| 29 | 23.787 | 3.7375 | 97.4 |
| 30 | 24.38 | 3.6479 | 43 |
| 31 | 24.99 | 3.5602 | 35.9 |
| 32 | 25.276 | 3.5207 | 11.1 |
| 33 | 26.18 | 3.4011 | 35.5 |
| 34 | 26.829 | 3.3203 | 13.1 |
| 35 | 27.069 | 3.2914 | 23.8 |
| 36 | 27.265 | 3.2681 | 37.1 |
| 37 | 28.492 | 3.1301 | 27.6 |
| 38 | 28.747 | 3.103 | 20.7 |
| 39 | 29.146 | 3.0614 | 14.3 |
| 40 | 29.531 | 3.0224 | 7.7 |
| 41 | 30.306 | 2.9468 | 19.7 |

TABLE 3-continued 10 days under the conditions of 40° C., 75% RH

| No. | 2θ angle (°) | Interplanar distance (Å) | Relative intensity (%) |
|---|---|---|---|
| 42 | 30.524 | 2.9262 | 14.5 |
| 43 | 31.749 | 2.8161 | 9.2 |
| 44 | 32.43 | 2.7585 | 8.5 |
| 45 | 33.232 | 2.6937 | 42.7 |
| 46 | 33.803 | 2.6495 | 16.2 |
| 47 | 34.177 | 2.6214 | 10.5 |
| 48 | 36.093 | 2.4865 | 7.7 |
| 49 | 38.204 | 2.3538 | 6.3 |
| 50 | 38.566 | 2.3325 | 11.2 |

In some embodiments of the present invention, the X-ray powder diffraction pattern of the crystal form A disposed and sampled (31 days) under the condition of 40° C., 75% RH is shown in FIG. 7.

In some embodiments of the present invention, the analysis data of the XPRD pattern of the crystal form A disposed and sampled (31 days) under the condition of 40° C., 75% RH is shown in Table 4.

TABLE 4

31 days under the conditions of 40° C., 75% RH

| No. | 2θ angle (°) | Interplanar distance (Å) | Relative intensity (%) |
|---|---|---|---|
| 1 | 8.78 | 10.0627 | 6.7 |
| 2 | 9.571 | 9.2328 | 19.4 |
| 3 | 9.887 | 8.9383 | 100 |
| 4 | 10.227 | 8.6424 | 8.2 |
| 5 | 10.641 | 8.3072 | 16.8 |
| 6 | 11.271 | 7.8438 | 17.5 |
| 7 | 11.939 | 7.4065 | 26.2 |
| 8 | 12.631 | 7.0025 | 14.7 |
| 9 | 13.048 | 6.7796 | 7.8 |
| 10 | 13.798 | 6.4128 | 13 |
| 11 | 14.116 | 6.2687 | 24.7 |
| 12 | 14.39 | 6.15 | 10.6 |
| 13 | 14.805 | 5.9786 | 84.4 |
| 14 | 15.259 | 5.8019 | 16 |
| 15 | 15.852 | 5.5859 | 14.4 |
| 16 | 16.627 | 5.3274 | 76.9 |
| 17 | 17.251 | 5.136 | 14.1 |
| 18 | 17.43 | 5.0836 | 6.7 |
| 19 | 18.655 | 4.7525 | 16.1 |
| 20 | 19.069 | 4.6502 | 11.8 |
| 21 | 19.332 | 4.5875 | 16.4 |
| 22 | 19.744 | 4.4929 | 35.9 |
| 23 | 20.199 | 4.3927 | 31.7 |
| 24 | 20.475 | 4.3341 | 7 |
| 25 | 20.851 | 4.2567 | 52.7 |
| 26 | 21.206 | 4.1862 | 16.4 |
| 27 | 22.154 | 4.0092 | 5.9 |
| 28 | 22.476 | 3.9525 | 64 |
| 29 | 22.928 | 3.8755 | 27.2 |
| 30 | 23.36 | 3.8048 | 19.1 |
| 31 | 23.777 | 3.7391 | 68.4 |
| 32 | 24.273 | 3.6639 | 29.1 |
| 33 | 24.941 | 3.5671 | 26 |
| 34 | 26.187 | 3.4002 | 16.9 |
| 35 | 27.216 | 3.2739 | 24.6 |
| 36 | 28.383 | 3.142 | 15.9 |
| 37 | 28.658 | 3.1124 | 11.9 |
| 38 | 29.054 | 3.0709 | 9.7 |
| 39 | 29.503 | 3.0251 | 5.9 |
| 40 | 30.219 | 2.9551 | 8.6 |
| 41 | 30.455 | 2.9327 | 8.2 |
| 42 | 31.29 | 2.8563 | 4.4 |
| 43 | 31.837 | 2.8085 | 3.6 |
| 44 | 32.409 | 2.7602 | 3.3 |
| 45 | 33.259 | 2.6916 | 22.4 |
| 46 | 33.79 | 2.6505 | 11.7 |
| 47 | 34.167 | 2.6221 | 6.1 |
| 48 | 36.088 | 2.4868 | 4.8 |
| 49 | 37.665 | 2.3862 | 2.8 |
| 50 | 38.137 | 2.3578 | 4.4 |
| 51 | 38.611 | 2.3299 | 3.1 |
| 52 | 39.74 | 2.2663 | 3.3 |

The present invention also provides a use of the crystal form A in the preparation of a medicament for treating breast cancer.

Technical Effect

The compound of the present invention does not contain crystal water or a crystal solvent, has good stability, has almost non-hygroscopicity, and has good prospects for preparation of medicaments.

Definition and Indication

Unless otherwise indicated, the following terms and phrases used herein are intended to have the following meanings. A particular term or phrase should not be considered uncertain or unclear without a special definition, but should be understood according to its ordinary meaning. When a trade name appears herein, it is intended to refer to its corresponding product or its active ingredient.

The intermediate compounds of the present invention can be prepared by a variety of synthetic methods well known to those skilled in the art, including the following specific embodiments, the embodiments formed by combining them with other chemical synthesis methods, and equivalent alternatives well known to those skilled in the art. Preferred embodiments include, but are not limited to, the embodiments of the present invention.

The chemical reactions of the specific embodiments of the present invention are performed in suitable solvents, and the solvents must be suitable for the chemical change of the present invention and the reagents and materials required for the same. In order to obtain the compound of the present invention, it is sometimes necessary for those skilled in the art to modify or select the synthetic steps or reaction schemes based on the existing embodiments.

The present invention will be described in detail below through embodiments, which do not imply any limitation to the present invention.

All solvents used in the present invention are commercially available and can be used without further purification.

The present invention uses the following abbreviations: min stands for minutes; rt stands for room temperature; THF stands for tetrahydrofuran; NMP stands for N-methylpyrrolidone; MeSO$_3$H stands for methanesulfonic acid; DME stands for 1,2-dimethoxyethane; DCM stands for dichloromethane; Xphos stands for 2-dicyclohexylphosphino-2', 4',6'-triisopropylbiphenyl; EtOAc stands for ethyl acetate; MeOH stands for methanol; acetone stands for propanone; 2-Me-THF stands for 2-methyltetrahydrofuran; IPA stands for isopropanol; RH stands for relative humidity.

Compounds are named by hand or Chemdraw® software, and commercially available compounds use the supplier catalog names thereof.

X-Ray Powder Diffractometer (XRPD)
Instrument model: Bruker D8 advance X-ray diffractometer
Test method: about 10-20 mg of sample was used for XRPD detection.
The detailed XRPD parameters were as follows:
X-ray Tube: Cu, Kα, (λ=1.54056 Å)
X-ray tube voltage: 40 kV, X-ray tube current: 40 mA
Divergence slit: 0.60 mm
Detector slit: 10.50 mm
Anti-scattering slit: 7.10 mm
Scanning range: 4-40 deg
Step diameter: 0.02 deg
Step length: 0.12 seconds
Rotation speed of sample tray: 15 rpm
Differential Scanning calorimeter (DSC)
Instrument model: TA Q2000 differential scanning calorimeter
Test method: samples (about 1 mg) were disposed in a DSC aluminum pan for testing, and heated at a heating rate of 10° C./min from 30° C. to 300° C. under the condition of 50 mL/min $N_2$.
Thermal Gravimetric Analyzer (TGA)
Instrument model: TA Q5000 thermal gravimetric analyzer
Test method: samples (2 mg to 5 mg) were disposed in a TGA platinum pot for testing and heated at a heating rate of 10° C./min under the condition of 50 mL/min $N_2$ from 30° C. (room temperature) to 300° C. or to a weight loss of 20%.
Dynamic Vapor Sorption (DVS)
Instrument model: SMS DVS Advantage dynamic vapor sorption analyzer
Test conditions: samples (10-15 mg) were disposed in the DVS sample tray for testing.
The detailed DVS parameters were as follows:
Temperature: 25° C.
Balance: dm/dt=0.01%/min (shortest: 10 min, longest: 180 min)
Drying: drying for 120 min at 0% RH
RH (%) test step: 10%
RH (%) test step range: 0%-90%-0%
The hygroscopicity evaluation is classified as follows:

| Hygroscopicity classification | Weight increase by hygroscopy* |
| --- | --- |
| deliquescence | absorbing enough water to form a liquid |
| very hygroscopic | ΔW % ≥ 15% |
| hygroscopic | 15% > ΔW % ≥ 2% |
| slightly hygroscopic | 2% > ΔW % ≥ 0.2% |
| Non-hygroscopic or almost non-hygroscopic | ΔW % < 0.2% |

*Weight increase by hygroscopy at 25 ± 1° C. and 80 ± 2% RH (ΔW %)

High Performance Liquid Chromatograph (HPLC)

| Equipment | Agilent 1200 high performance liquid chromatograph |
| --- | --- |
| Chromatographic column | Waters Xbridge shield RP18 (150 mm*4.6 mm, 3.5 um) |
| Mobile phase A | 0.1% THF aqueous solution |
| Mobile phase B | 100% acetonitrile |
| Flow rate | 0.8 mL/min |
| Injection volume | 10 μl |
| Detection wavelength | 220 nm |
| Column temperature | 40° C. |
| Diluent | acetonitrile:water (2:1) |

| Gradient elution process | Time (minute) | Mobile phase A (%) | Mobile phase B (%) |
| --- | --- | --- | --- |
| | 0.00 | 90 | 10 |
| | 50.00 | 10 | 90 |
| | 55.00 | 10 | 90 |
| | 57.00 | 90 | 10 |
| | 62.00 | 90 | 10 |

Constant Temperature and Humidity Test Chamber
Manufacturer: Binder
Instrument model: KBF-240

DETAILED DESCRIPTION OF THE PREFERRED EMBODIMENT

Figure 1:
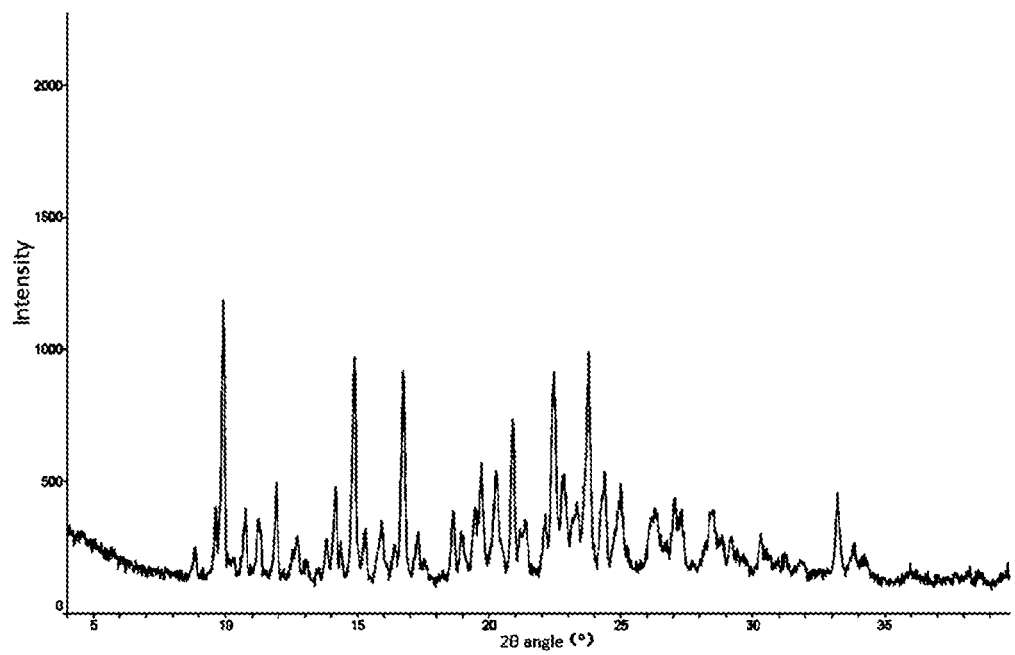
FIG. 1 is an XRPD pattern under Cu-Kα radiation of the crystal form A of the compound of formula (I).

In order to better understand the content of the present invention, the following examples further illustrate the present invention, but the present invention is not limited thereto.

Embodiment 1: Preparation for a Compound of Formula (I)

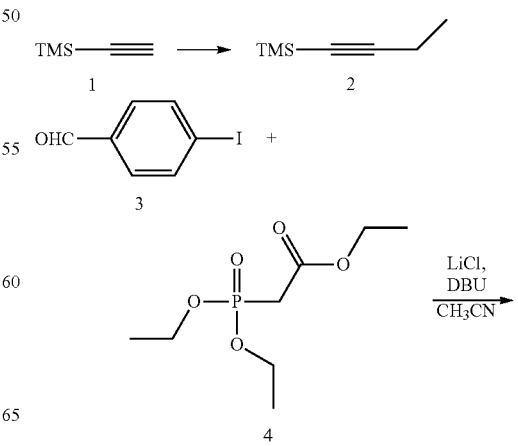

-continued

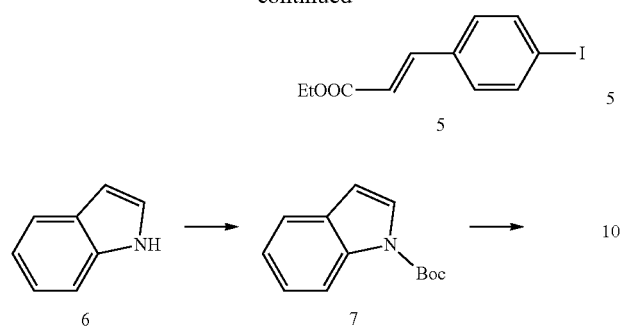

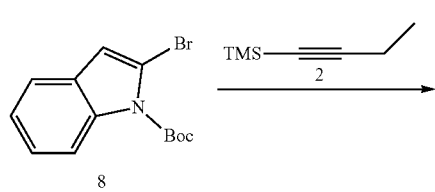

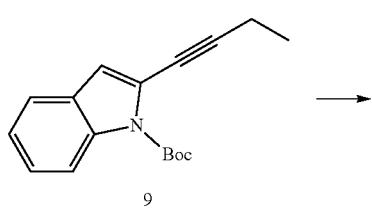

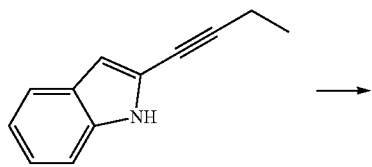

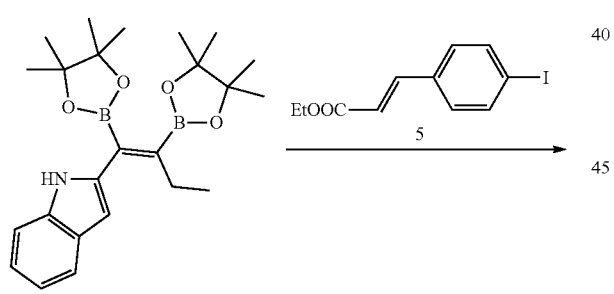

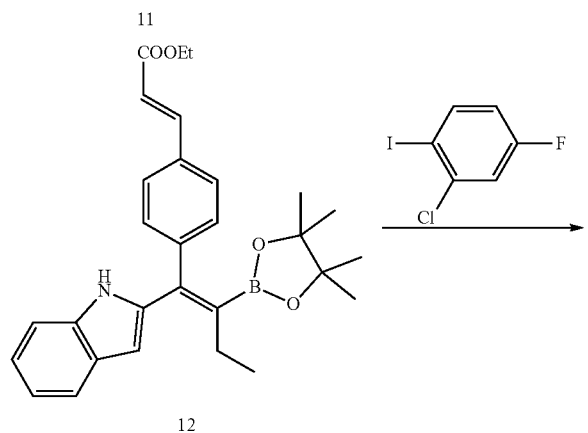

-continued

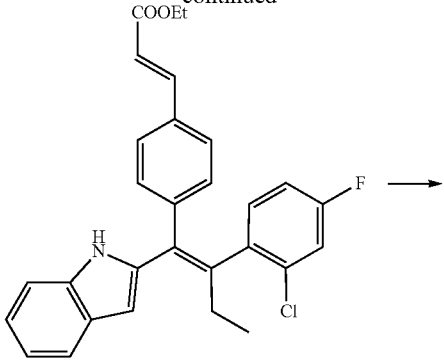

13

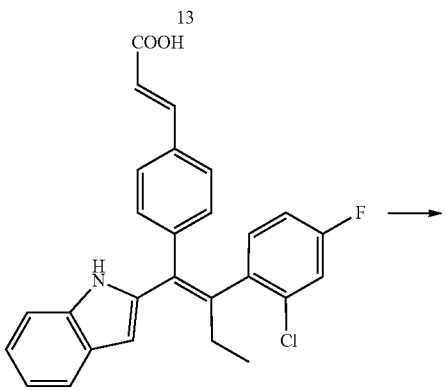

14

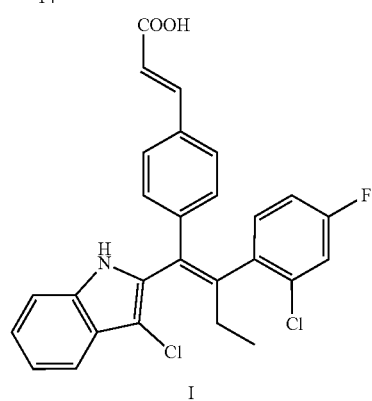

I

Step A: N'-butyl lithium (2.5M, 428.40 mL, 1.05 eq) was slowly added dropwise (for 1 hour) to a solution of 1 (100.00 g, 1.02 mol, 140.85 ml, 1.00 eq) in tetrahydrofuran (500 mL) at −75° C. under nitrogen atmosphere. The obtained reaction solution was heated to 0° C. and stirred for 10 minutes, and then cooled to −75C. Hexamethyl phosphoryl triamine (201.06 g, 1.12 mol, 197.12 mL, 1.10 eq) was added (for 1 hour) thereto. The obtained reaction solution was stirred at −75° C. for 1 hour, then added (for 1 hour) with iodoethane (198.86 g, 1.27 mol, 101.98 mL, 1.25 eq), heated to 20° C. to react for 10 hours, added with 400 mL water, and partitioned to obtain organic phase. The obtained organic phase was washed with 400 mL water for three times, dried with anhydrous sodium sulfate, filtered, and separated by distillation to obtain product 2.

Step B: triethyl phosphoryl acetate 4 (11.60 g, 51.72 mmol, 10.26 mL, 1.20 eq) and lithium chloride (3.65 g, 86.20 mmol, 1.77 mL, 2.00 eq) were added to a solution of 3 (10.00 g, 43.10 mmol, 1.00 eq) in 100 mL acetonitrile. An acetonitrile solution of DBU (8.53 g, 56.03 mmol, 8.45 mL, 1.30 eq) was added dropwise (for 30 minutes) at 0° C. under nitrogen atmosphere. The obtained reaction solution was allowed to react at 15° C. for 1 hour, then added with 100 mL water, and partitioned. The obtained aqueous phase was extracted twice with 70 mL of dichloromethane. The combined organic phase was dried with anhydrous sodium sulfate, filtered, and concentrated to obtain crude product. The crude product was separated by silica gel column chromatography (PE:EA=100:1-30:1) to obtain product 5.

Step C: dimethylaminopyridine (3.65 g, 29.88 mmol, 0.10 eq) and Boc$_2$O (68.46 g, 313.70 mmol, 72.07 mL, 1.05 eq) were added to a solution of 6 (35.00 g, 298.76 mmol, 1.00 eq) in 400 mL dichloromethane. The obtained reaction solution was allowed to react at 20° C. for 12 hours, and then extracted twice with 400 mL ammonium chloride solution. The organic layer was dried with anhydrous sodium sulfate, filtered and concentrated to obtain product 7.

Step D: lithium diisopropylamide (2M, 75.95 mL, 1.10 eq) was slowly added to a solution (400 mL) of 7 (30.00 g, 138.08 mmol, 1.00 eq) in tetrahydrofuran at −75° C. under nitrogen protection. The obtained reaction solution was stirred at −75° C. for 30 minutes, then added with bromocyanide (55.40 g, 523.04 mmol, 38.47 mL, 3.79 eq), heated to 15° C. to react for 12 hours, added with 400 mL water, and partitioned. The obtained organic phase was washed with 300 mL water for three times. The organic layer was dried with anhydrous sodium sulfate and filtered to obtain a crude product. The crude product was separated by silica gel column chromatography (PE:EA=1:0-50:1) to obtain product 8.

Step E: cesium carbonate (85.81 g, 263.38 mmol, 2.00 eq), cuprous iodide (1.25 g, 6.58 mmol, 0.05 eq), palladium acetate (1.48 g, 6.58 mmol, 0.05 eq) and 1,1'-bis(diphenylphosphino)ferrocene (3.65 g, 6.58 mmol, 0.05 eq) were added to 300 mL solution of 8 (39.00 g, 131.69 mmol, 1.00 eq) in N,N-dimethylacetamide, and then 2 (33.26 g, 263.38 mmol, 2.00 eq) was added thereto under nitrogen protection. The obtained reaction solution was allowed to react at 80° C. for 12 hours, then added with 1 L ethyl acetate and 1 L water, filtered, and partitioned. The obtained organic layer was extracted with 1 L water for 3 times, dried with anhydrous sodium sulfate, filtered and concentrated to obtain a crude product. The crude product was separated by silica gel column chromatography (PE:EA=1:0-30:1) to obtain product 9.

Step F: potassium carbonate (69.27 g, 501.25 mmol, 5.00 eq) was added to a solution of 9 (27.00 g, 100.25 mmol, 1.00 eq) in 300 mL methanol and 15 mL water. The reaction solution was allowed to react at 70° C. for 12 hours, then filtered, concentrated, added with 300 mL ethyl acetate, and extracted twice with 300 mL water. The organic layer was dried with anhydrous sodium sulfate, filtered and concentrated to obtain a crude product. The crude product was separated by silica gel column chromatography (PE:EA=100:1-30:1) to obtain product 10.

Step G: bis(pinacolato)diboron (4.50 g, 17.73 mmol, 1.00 eq) and tetrakis(triphenylphosphine)platinum (1.10 g, 886.50 umol, 0.05 eq) were added to a solution of 5 (3.00 g, 17.73 mmol, 1.00 eq) in 30 mL dimethyltetrahydrofuran. The reaction solution was allowed to react at 70° C. under nitrogen protection for 5 hours, and then cooled to room temperature. 6 in the reaction solution can be used directly in the reaction of next step without purification.

Step H: cesium carbonate (11.55 g, 35.44 mmol, 2.00 eq), compound 5 (4.28 g, 14.18 mmol, 0.80 eq) and palladium (II)bis(triphenylphosphine) dichloride (622.02 mg, 886.00 umol, 0.05 eq) were added to a solution of 10 (7.50 g, 17.72 mmol, 1.00 eq) in 70 mL dimethyltetrahydrofuran and 3 mL water at 0. The reaction solution was allowed to react at 15° C. under nitrogen protection for 12 hours. 11 in the reaction solution can be used directly in the reaction of next step without purification.

Step I: 2-chloro-4-fluoroiodobenzene (9.03 g, 35.22 mmol, 2.00 eq), potassium hydroxide solution (4M, 22.01 mL, 5.00 eq) and palladium(II)bis(triphenylphosphine) dichloride (617.94 mg, 880.50 umol, 0.05 eq) were added to a solution of 11 (8.30 g, 17.61 mmol, 1.00 eq) in 100 mL dimethyltetrahydrofuran. The reaction solution was allowed to react at 70° C. under nitrogen protection for 12 hours, and filtered with celite, and the filtrate was extracted twice with 100 mL saturated saline. The organic layer was dried with anhydrous sodium sulfate, filtered and concentrated to obtain a crude product. The crude product was separated by silica gel column chromatography (PE:EA=40:1-10:1) to obtain product 13.

Step J: lithium hydroxide (1.33 g, 55.73 mmol, 10.00 eq) was added to a mixed solution of 13 (4.50 g, 5.57 mmol, 1.00 eq) in 30 mL methanol, 30 mL tetrahydrofuran and 10 mL water. The reaction solution was allowed to react at 35° C. for 1 hour and added with 30 mL water. Then the pH thereof was adjusted to 5 with a 1M hydrochloric acid solution, and the obtained reaction solution was extracted twice with 50 mL ethyl acetate. The combined organic layers were extracted twice with 60 mL water. The organic layer was dried with anhydrous sodium sulfate, filtered and concentrated to obtain a crude product. The crude product was separated by preparative HPLC (formic acid system) to obtain 14.

Step K: compound 14 (150.00 mg, 336.39 umol, 1.00 eq) and N-chlorosuccinimide (53.90 mg, 403.67 umol, 1.20 eq) were dissolved in 5 mL acetonitrile. The reaction solution was stirred at 15° C. for 6 hours under nitrogen protection. After the reaction was completed, the reaction solution was concentrated and separated by the formic acid system to obtain product I.

$^1$H NMR (400 MHz, DMSO-d$_6$) 11.51 (s, 1H), 7.50 (d, J=8.0 Hz, 1H), 7.47-7.37 (m, 5H), 7.29 (dd, J=6.4, 8.4 Hz, 1H), 7.22-7.09 (m, 3H), 7.01 (d, J=8.4 Hz, 2H), 6.41 (d, J=16.4 Hz, 1H), 2.49-2.36 (m, 2H), 0.89 (t, J=7.6 Hz, 3H).

Embodiment 2: Preparation for Crystal Form A of the Compound of Formula (I)

The compound of formula (I) (5.0 g, 10.35 mmol) was stirred and heated to reflux in 100 mL mixture of methanol and water (volume ratio, methanol:water=4:1) until the solid was completely dissolved, naturally cooled to 15° C., and filtered. The filter cake was washed with 10 mL mixture of methanol and water (volume ratio, methanol:water=4:1), and dried under vacuum at 50° C. to obtain crystal form A of the compound of formula (I).

The compound of formula (I) (5.0 g, 10.35 mmol) was stirred and heated to reflux for 20 hours in 20 mL mixture of methanol and water (volume ratio, methanol:water=1:1), naturally cooled to 15° C., and filtered. The filter cake was washed with 2 mL mixture of methanol and water (volume ratio, methanol:water=1:1), and dried under vacuum at 50° C. to obtain crystal form A of the compound of formula (I).

Embodiment 3: Study on the Hygroscopicity of the Crystal Form A of Compound of Formula (I)

Figure 4:
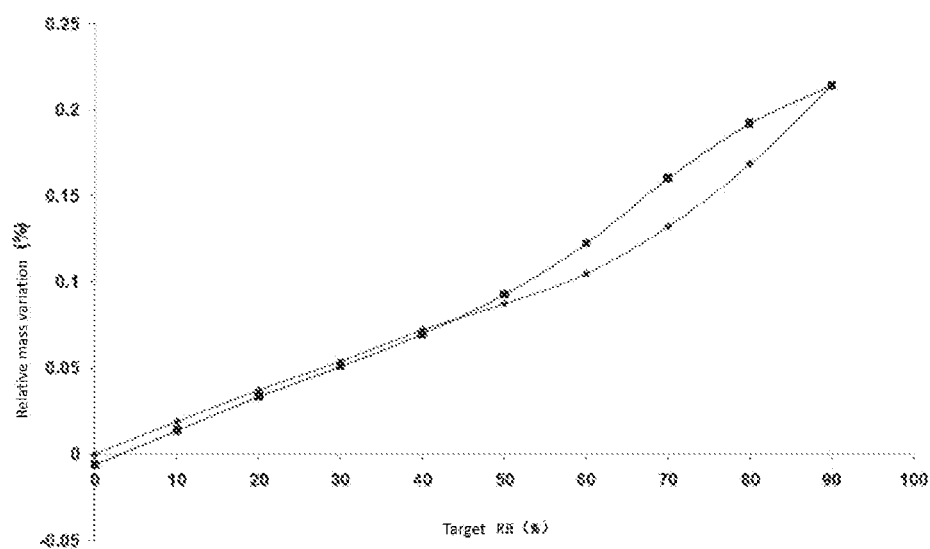
FIG. 4 is a DVS pattern of the crystal form A of the compound of formula (I). The square dotted line represents the desorption curve, and the rhombus dotted solid line represents the adsorption curve.

Experiment Material:
SMS DVS Advantage dynamic vapor sorption analyzer
Experiment Method:
An appropriate amount of the crystal form A of compound of formula (I) was placed in a DVS sample tray for DVS analysis.
Experiment Results:
The DVS pattern of the crystal form A of compound of formula (I) was shown in FIG. 4, ΔW=0.1687%.
Experiment Conclusion:
The weight increase caused by hygroscopy of free acid crystal form III of the crystal form A of compound of formula (I) at 25° C./80% RH is 0.1687%, which is almost non-hygroscopic.

Embodiment 4: Solid Stability Test of the Crystal Form A of the Compound of Formula (I) Under High Humidity and Light Irradiation Conditions Experiment Purpose:
The stability of the crystal form A of the compound of formula (I) under high humidity (room temperature/relative humidity 92.5%, exposed) and light irradiation (1ICH, total illuminance=1.2×10$^6$ Lux·hr/near ultraviolet=200 w·hr/m$^2$, exposed) conditions was investigated.
Experiment Method:
The crystal form A of the compound of formula (I) (2 samples of 10 mg each for analysis of related substances, and 1 sample of appropriate amount for detection of crystal form stability) was placed on the bottom of a glass sample bottle, and spread out into a thin layer. The bottles containing samples placed under high humidity condition were sealed with aluminum foil. Small holes were made in the aluminum foil to ensure that the samples can fully contact with the ambient air. The samples were tested on the 10th day. The bottles containing samples placed under light condition were left open and the samples were exposed to a light source, and tested after being irradiated enough energy. The test results were compared with the initial test results on day 0.
Experiment results: see Tables 5 and 6 below.

TABLE 5 solid stability test of the crystal form A of the compound of formula (I)

| Test conditions | Time point | Crystal form (XRPD) |
|---|---|---|
| — | 0 day | Crystal form A |
| High humidity (room temperature/relative humidity 92.5%, exposed) | 10th day | Crystal form A |
| Light irradiation (1ICH, exposed) | — | Crystal form A |

Experiment conclusion: the crystal form A of the compound of formula (I) is stable under high humidity and light irradiation condition.

Figure 5:
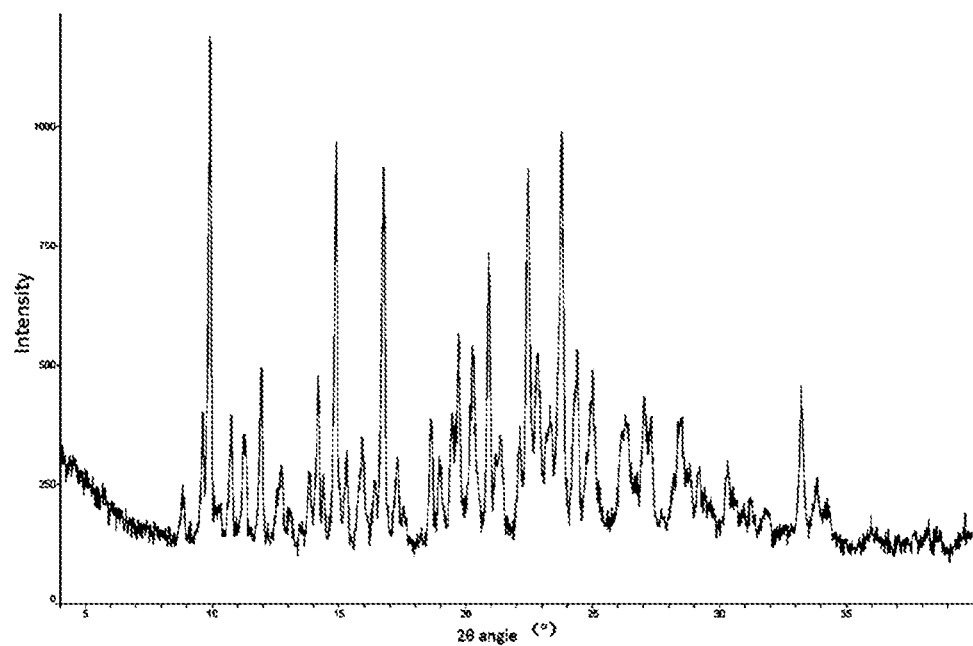
FIG. 5 is an XRPD pattern under Cu-Kα radiation of the crystal form A of the compound of formula (I) disposed and sampled (0 day) under the condition of 40° C., 75% RH.
Figure 6:
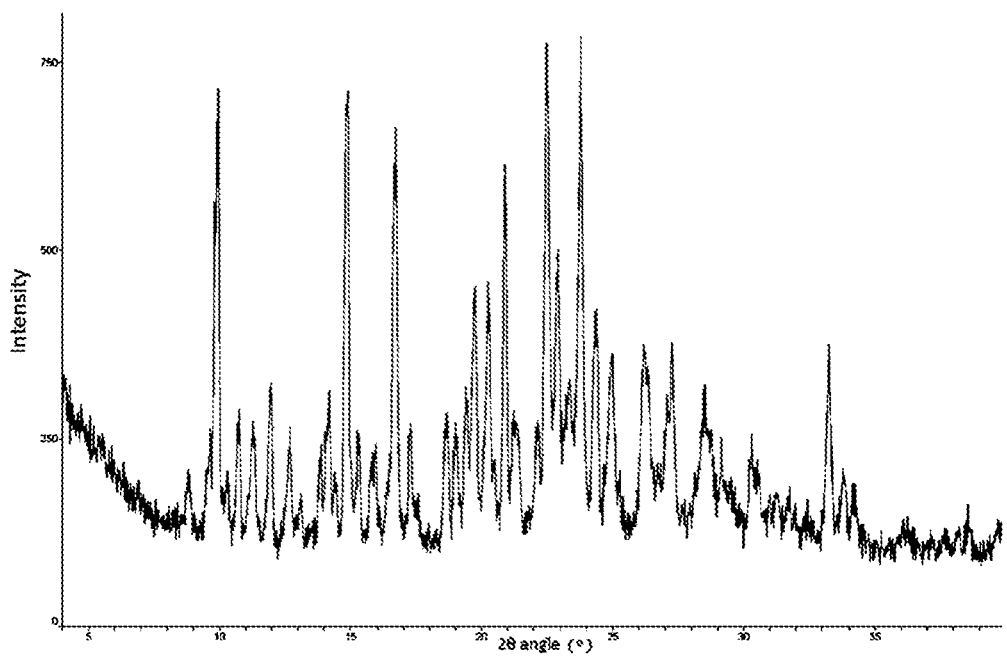
FIG. 6 is an XRPD pattern under Cu-Kα radiation of the crystal form A of the compound of formula (I) disposed and sampled (10th day) under the condition of 40° C., 75% RH.
Figure 7:
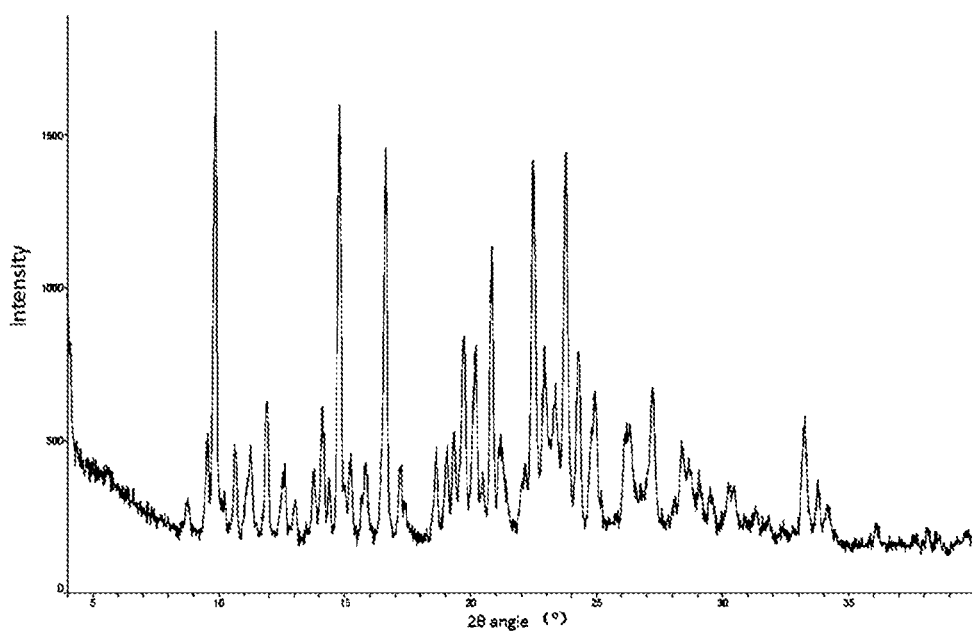
FIG. 7 is an XRPD pattern under Cu-Kα radiation of the crystal form A of the compound of formula (I) disposed and sampled (31th day) under the condition of 40° C., 75% RH.

Embodiment 5: Long-Term Crystal Form Stability Test of the Crystal Form A of the Compound of Formula (I) Under High Temperature and High Humidity Conditions The XRPD of the crystal form A of the compound disposed under the condition of 40° C., 75% RH was sampled and detected at different time points (10th day, 31th day). The crystal form A of the compound was stored in a refrigerator at −20° C. as a reference. The XRPD results were shown in FIGS. 5, 6, and 7.

Experiment conclusion: the crystal form A of the compound of formula (I) is stable under high temperature and high humidity conditions for a long time.

What is claimed is:
1. Crystal form A of a compound of formula (I), characterized by X-ray powder diffraction pattern having characteristic diffraction peaks at the following 2θ angles: 9.921±0.2°, 11.949±0.2°, 14.895±0.2°, 16.753±0.2°, 19.713±0.2°, 20.9±0.2°, 22.45±0.2°, and 23.78±0.2°,

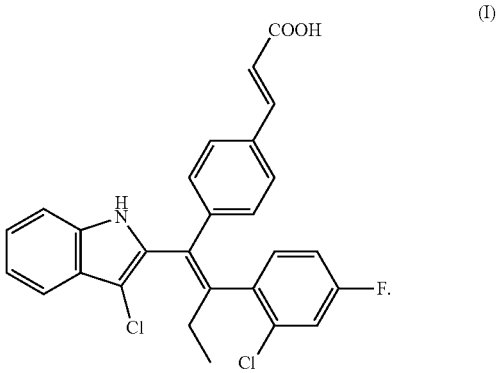 [SMILES: CC/C(=C(/c1ccc(/C=C/C(=O)O)cc1)c1[nH]c2ccccc2c1Cl)c1ccc(F)cc1Cl]

(I)

2. The crystal form A according to claim 1, characterized by X-ray powder diffraction pattern having characteristic diffraction peaks at the following 2θ angles: 9.921±0.2°, 10.751±0, ±02°, 11.949±0.2°, 14.169±0.2°, 14.895±0.2°, 16.753±0.2°, 19.713±0.2°, 20.268.2°, 20.9±0.2°, 22.45±0.2°, 23.78±0.2°, and 24.39±0.2°.

3. The crystal form A according to claim 2, characterized by X-ray powder diffraction pattern shown in FIG. 1 in the description.

TABLE 6

HPLC analysis results of solid stability test of the crystal form A of the compound of formula (I)

| | Relative retention time | | | | | | Total content of related substances (%) | Purity (%) |
|---|---|---|---|---|---|---|---|---|
| | 0.88 | 0.97 | 0.98 | 1.02 | 1.04 | 1.05 | | |
| 0 day | | | 0.21 | | 0.36 | 0.30 | 0.87 | 96.99 |
| High humidity, 10 days | | | 0.22 | | 0.23 | 0.31 | 0.77 | 107.62 |
| Light irradiation | 0.05 | 0.22 | 0.17 | 0.23 | 0.13 | 0.17 | 0.98 | 101.09 |

4. The crystal form A according to claim 1, characterized by differential scanning calorimetric curve having an endothermic peak at 195.45° C.±3° C.

Figure 2:
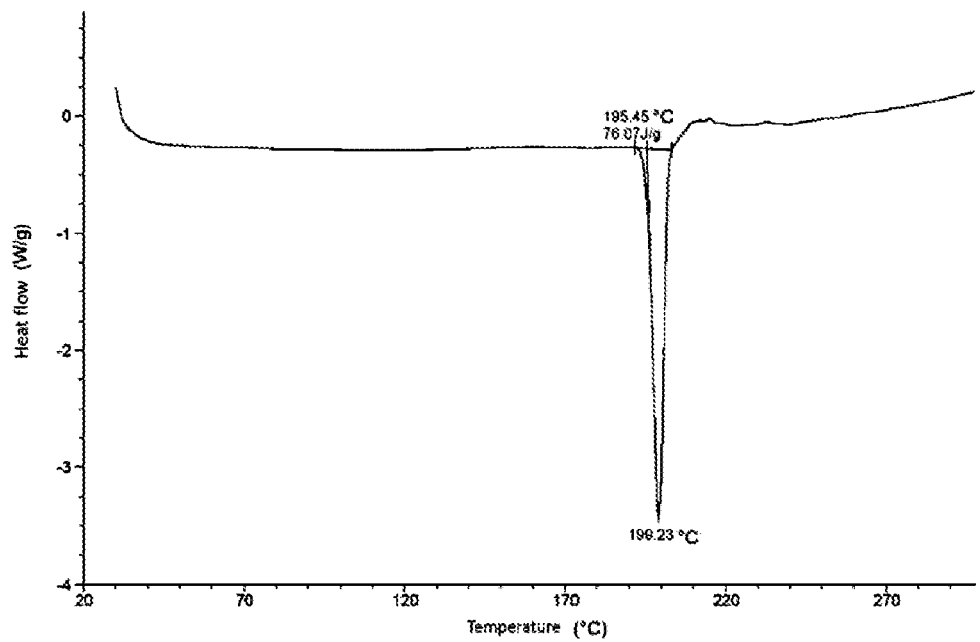
FIG. 2 is a DSC pattern of the crystal form A of the compound of formula (I).

5. The crystal form A according to claim 4, characterized by differential scanning calorimetric curve pattern shown in FIG. 2 in the description.

6. The crystal form A according to claim 1, characterized by thermogravimetric curve having a weight loss of 0.1919%±0.2% at 191.73±3° C.

Figure 3:
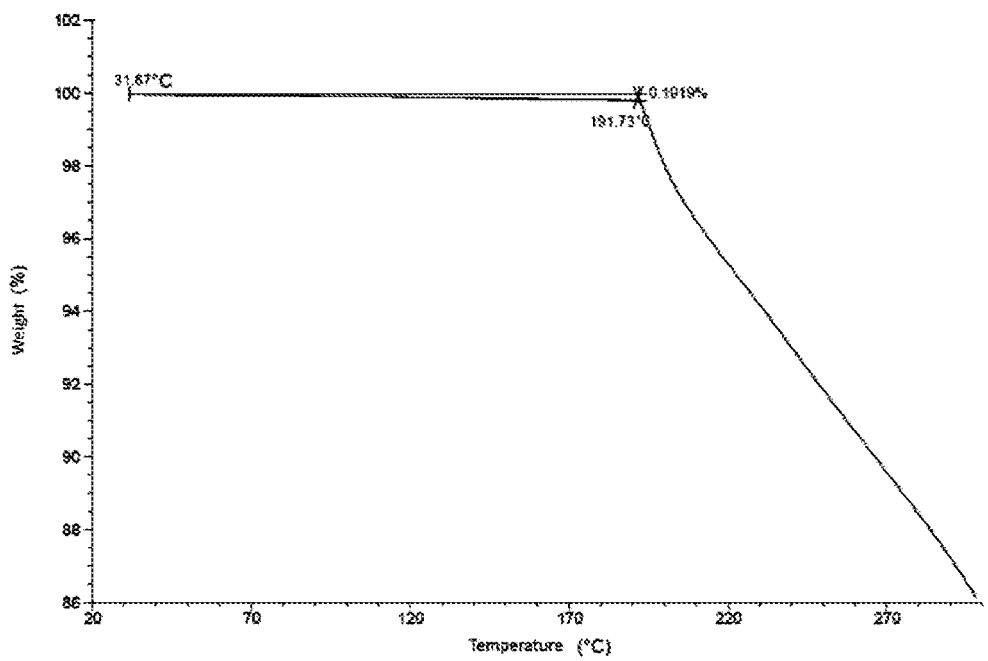
FIG. 3 is a TGA pattern of the crystal form A of the compound of formula (I).

7. The crystal form A according to claim 6, characterized by thermogravimetric curve pattern shown in FIG. 3 in the description.

8. A preparation method for crystal form A of a compound of formula (I), comprising:
  (a) adding the compound of formula (I) to a solvent, stirring, heating, refluxing, naturally cooling to 10° C. to 25° C. after dissolution;
  (b) filtering, washing the filter cake with a solvent; and
  (c) vacuum drying at 50° C.;
  wherein the solvent is selected from methanol, ethanol, isopropanol, a mixed solvent of ethanol and water, a mixed solvent of methanol and water, or a mixed solvent of isopropanol and water;

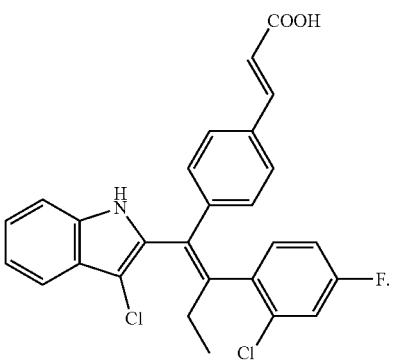

9. The method according to claim 8, wherein the volume ratio of methanol to water in the mixed solvent is (1-4):1.

10. The method according to claim 9, wherein the volume ratio of methanol to water in the mixed solvent is 1:1.

11. A method for treating breast cancer in a subject in need thereof, comprising administering an effective amount of the crystal form A according to claim 1 to the subject.

12. A method for treating breast cancer in a subject in need thereof, comprising administering an effective amount of the crystal form prepared by the method according to claim 8 to the subject.

* * * * *